United States Patent [19]
Kane et al.

[11] Patent Number: 5,441,480
[45] Date of Patent: Aug. 15, 1995

[54] SURGICAL TRACTION DEVICE

[76] Inventors: John P. Kane; Hector A. Alvarez, both of 1316 F. Gateview Ave., T.I. San Francisco, Calif. 94130

[21] Appl. No.: 199,426

[22] Filed: Feb. 22, 1994

[51] Int. Cl.⁶ .................................................. A61F 5/00
[52] U.S. Cl. ........................................ 602/36; 602/5; 602/21; 128/879; 5/647
[58] Field of Search ............... 602/5, 21, 22, 32, 35, 602/36, 40; 428/878, 879, 880; 601/40; 606/241; 5/623, 646, 647, 601; D24/171, 183, 184, 190; 254/217, 223; 242/389, 396.2, 396.4; 273/29 BC, 29 BD, 73 B

[56] References Cited
U.S. PATENT DOCUMENTS

| | | | |
|---|---|---|---|
| 2,524,406 | 10/1950 | Swenson | 254/217 |
| 3,096,884 | 7/1963 | Leshner | 242/396.4 |
| 3,629,581 | 12/1971 | Smith | 5/601 |
| 4,057,220 | 11/1977 | Kudlacek | 242/396.4 |
| 4,483,330 | 11/1984 | Jacobsen et al. | 602/32 |
| 4,858,903 | 8/1989 | Tari et al. | 5/623 |
| 5,156,168 | 10/1992 | Canterner | 602/21 |

*Primary Examiner*—Richard J. Apley
*Assistant Examiner*—Jeanne M. Clark

[57] ABSTRACT

Apparatus for applying traction forces to the fingers of a patient during surgery comprising a traction box, the traction box having wires extending therefrom with their outboard ends connecting to finger traps, by means of an "S" hook, for holding the fingers of the patient and with their inboard ends extending to within the traction box.

5 Claims, 3 Drawing Sheets

000
SURGICAL TRACTION DEVICE

BACKGROUND OF THE INVENTION

1. Field of the Invention

The present invention relates to a surgical traction device and more particularly pertains to apparatus for holding the fingers of a patient during surgery whereby traction forces are applied to the hand, wrist and forearm of the patient.

2. Description of the Prior Art

The use of surgical devices are known in the prior art. More specifically, surgical devices heretofore devised and utilized for the purposes of applying traction forces to a patient are known to consist basically of familiar, expected and obvious structural configurations, notwithstanding the myriad of designs encompassed by the crowded prior art which have been developed for the fulfillment of countless objectives and requirements.

As illustrated in the prior art, a wide variety of devices have been devised for supporting the patients forearm, wrist hand and fingers during surgery. Note for example U.S. Pat. No. 4,858,903 to Tari featuring a forearm support and hand support with flexible tensionable cables carrying finger-fixing thimbles.

U.S. Pat. Nos. 4,564,180 to Agee and 4,054,282 to Hamer disclose single tables for the arms of patients during an operation.

U.S. Pat. No. 4,807,864 to Young discloses an operating table for a hand of a patient with tie down mechanisms.

U.S. Pat. No. 3,746,332 to Hakstian discloses a device in the form of a work bench for encasing a wearers fingers, hand, wrist and forearm during surgery.

U.S. Pat. No. 5,074,291 to Carter discloses a surgical table for the forearm, wrist, hand and fingers wherein a plurality of fingers are held in traction but the traction is of a force common to the plural fingers and not the individual fingers.

In this respect, the device according to the present invention substantially departs from the conventional concepts and designs of the prior art, and in so doing provides an apparatus primarily developed for the purpose of applying individual forces to the fingers of a patient during orthopedic surgery.

Therefore, it can be appreciated that there exists a continuing need for new and improved surgical devices which can be used for applying traction forces to the individual fingers. In this regard, the present invention substantially fulfills this need.

SUMMARY OF THE INVENTION

In view of the foregoing disadvantages inherent in the known types of surgical devices now present in the prior art, the present invention provides an improved traction force applicator when the same can be utilized for individual forces for the individual fingers. As such, the general purpose of the present invention, which will be described subsequently in greater detail, is to provide a new and improved surgical traction devices apparatus and method which has all the advantages of the prior art traction devices and none of the disadvantages.

To attain this, the present invention essentially comprises apparatus for applying traction forces to the fingers, wrist and forearm of a patient during orthoscopic surgery comprising, in combination a cradle for the arm of the patient, the cradle being radiolucent; a clamp adapted to releasable secure the cradle to an operating table during surgery; a traction box secure with respect to the cradle, the traction box having wires extending therefrom with their outboard ends extending over the cradle and connecting to finger traps, by means of an "S" hook, for holding the fingers of the patient and with their inboard ends extending to within the traction box; tensioning means within the traction box, the tensioning means including a shaft supported about a horizontal axis perpendicular to the wires, a plurality of spools mounted for rotation upon the shaft with the inboard end of each wire secured to an associated spool, a rachet wheel coupled to each spool and a pawl operatively coupled to each rachet wheel; control means operatively coupled to each spool and rachet wheel, the control means including a wrench to pivot the axis of the pawl about an axis consistent with the axis of the shaft to move the pawl in a reciprocating arcuate path to advance its associated rachet wheel and spool to wind up its associated wire and to apply a traction force to a finger of a patient, each control means also including a rod extending through its associated wrench to pull the pawl against the action of a spring away from its ratchet wheel for releasing the traction; and a gauge associated with each spool to sense and display the pressure applied to each finger through its wire, spool and wrench.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

It is therefore an object of the present invention to provide a new and improved surgical traction device which has all the advantages of the prior art surgical aids and none of the disadvantages.

It is another object of the present invention to provide a new and improved surgical traction device which may be easily and efficiently manufactured and marketed.

It is a further object of the present invention to provide a new and improved surgical traction device which is of a durable and reliable construction.

An even further object of the present invention is to provide a new and improved surgical traction device which is susceptible of a low cost of manufacture with regard to both materials and labor, and which accordingly is then susceptible of low prices of sale to the health care industry thereby making such surgical devices economically available to the medical market.

Still yet another object of the present invention is to provide a new and improved surgical traction device which provides in the apparatuses and methods of the prior art some of the advantages thereof, while simultaneously overcoming some of the disadvantages normally associated therewith.

Still another object of the present invention is to provide a new and improved surgical traction device.

Yet another object of the present invention is to apply traction forces of individual magnitudes to the individual fingers of a patient undergoing orthoscopic surgery for the hand, wrist or forearm.

Even still another object of the present invention is to facilitate orthopedic surgery by applying forces of traction to the individual fingers of the patient.

Even still another object of the present invention is to determine and display the traction forces applied to each finger of the patient during surgery.

Even still another object of the present invention is to effective release of traction forces to the fingers of a patient during surgery through quick release mechanisms.

It is an object of the present invention to provide an apparatus for applying traction forces to the fingers of a patient during surgery comprising a traction box, the traction box having wires extending therefrom with their outboard ends connecting to finger traps, by means of an "S" hook, for holding the fingers of the patient and with their inboard ends extending to within the traction box; tensioning means within the traction box, the tensioning means including a shaft supported about an axis perpendicular to the wires, a plurality of spools mounted for rotation upon the shaft with the inboard end of each wire secured to an associated spool, a rachet wheel coupled to each spool and a pawl operatively coupled to each rachet; and control mechanisms operatively coupled to each spool and rachet wheel the control means including a wrench to pivot the pawl about an axis consistent with the access of the shaft to move the pawl in a reciprocating arcuate movement to advance its associated rachet wheel and spool to wind up its associated wire for applying a traction force to a finger of a patient.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
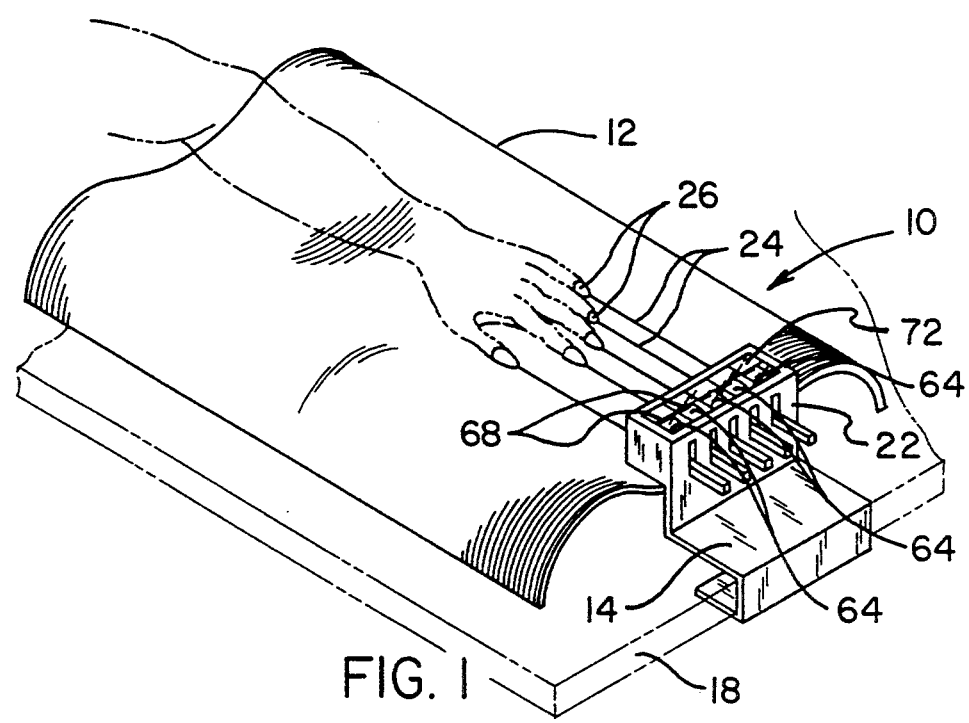
FIG. 1 is a prospective illustration of the title constructed in accordance with the present invention and illustrating the forearm, wrist, hand and fingers of the patient.
Figure 2:
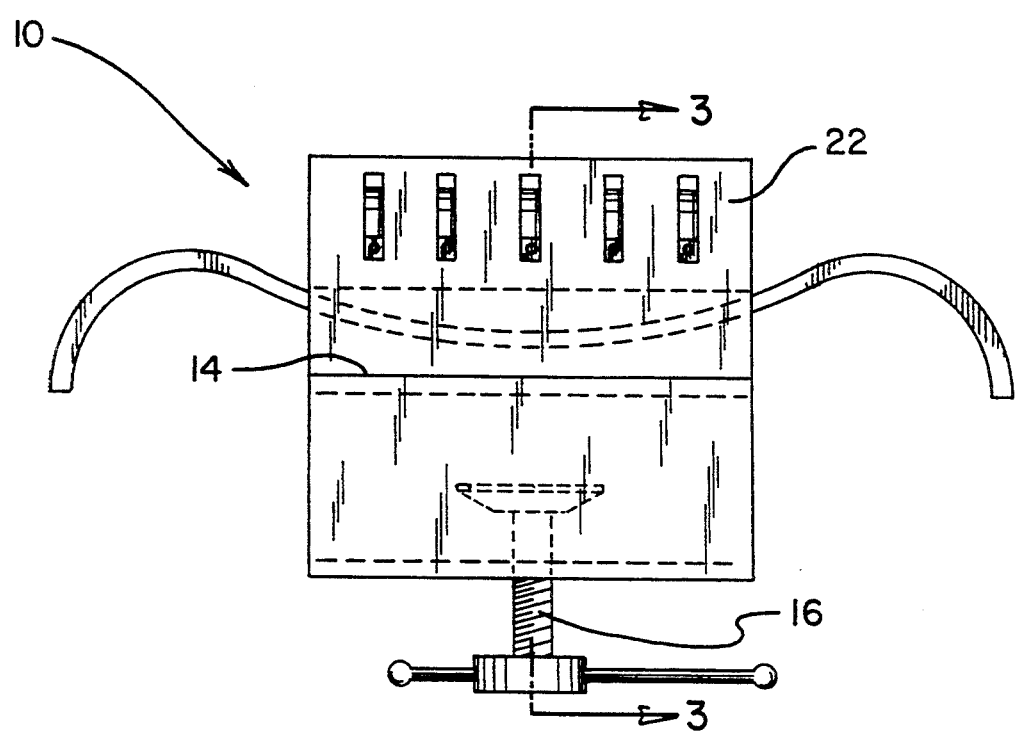
FIG. 2 is a perspective view of the apparatus shown in FIG. 1 without the patient's hand and without the supporting table.
Figure 3:
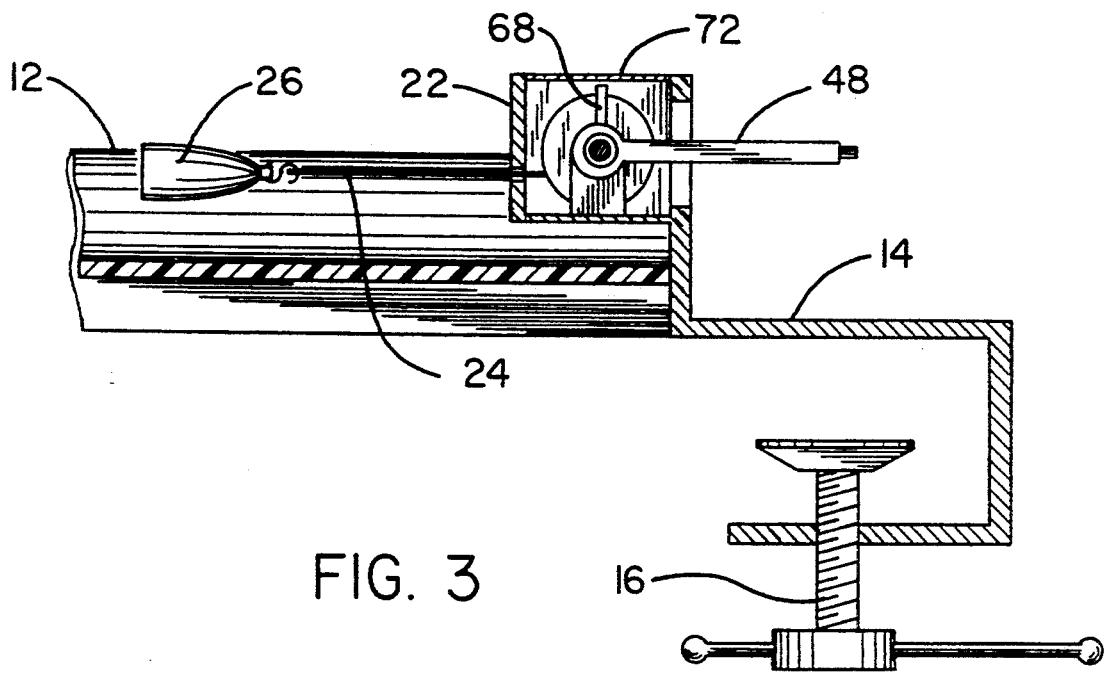
FIG. 3 is a sectional view of the device shown in FIGS. 1 and 2 taken along line 3—3 of FIG. 2.
Figure 4:
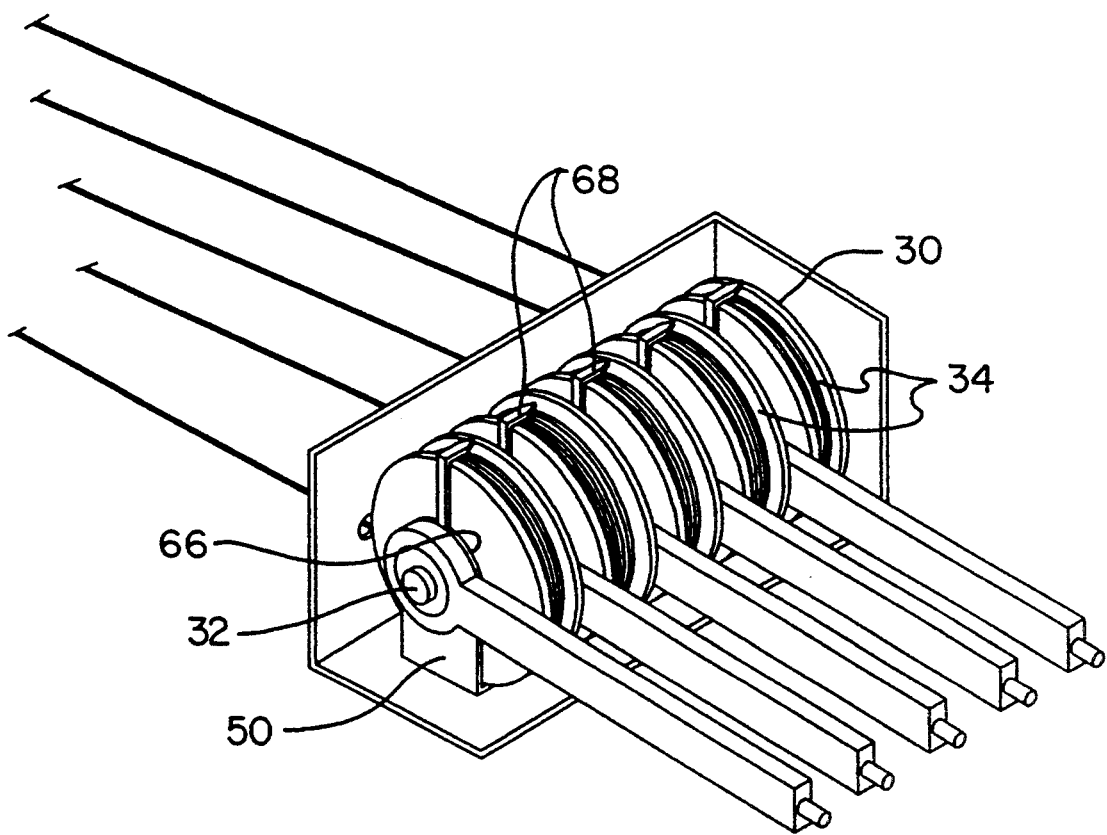
FIG. 4 is a view of the traction box and interior mechanisms with a portion of the box removed to show certain internal constructions thereof.
Figure 5:
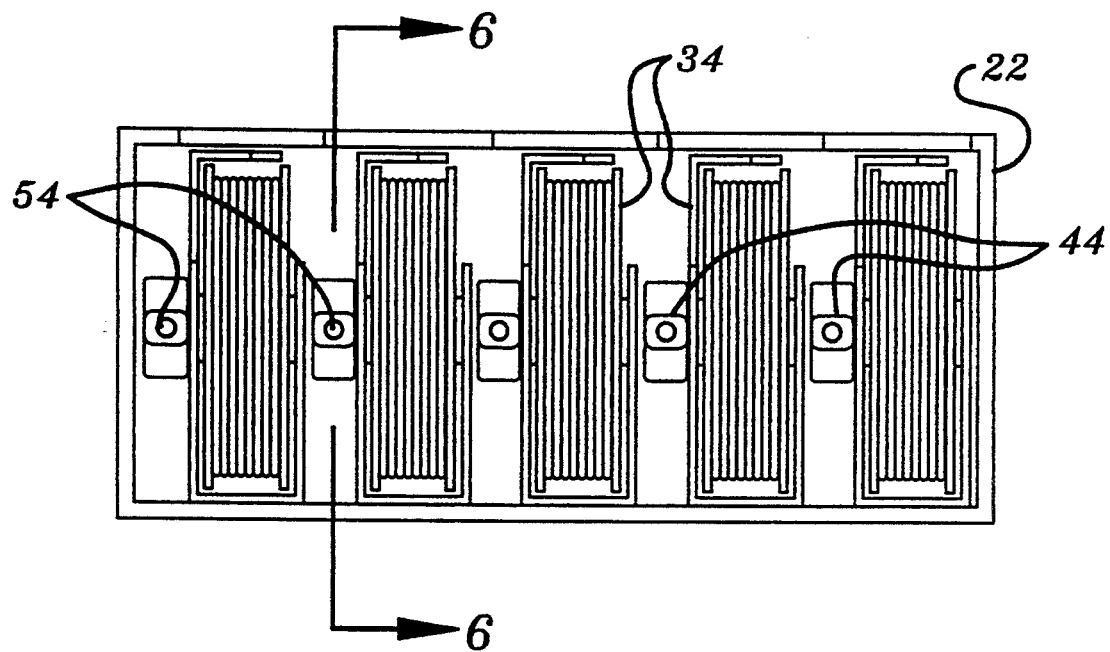
FIG. 5 is a planned view of the interior of the traction box shown in FIG. 4.
Figure 6:
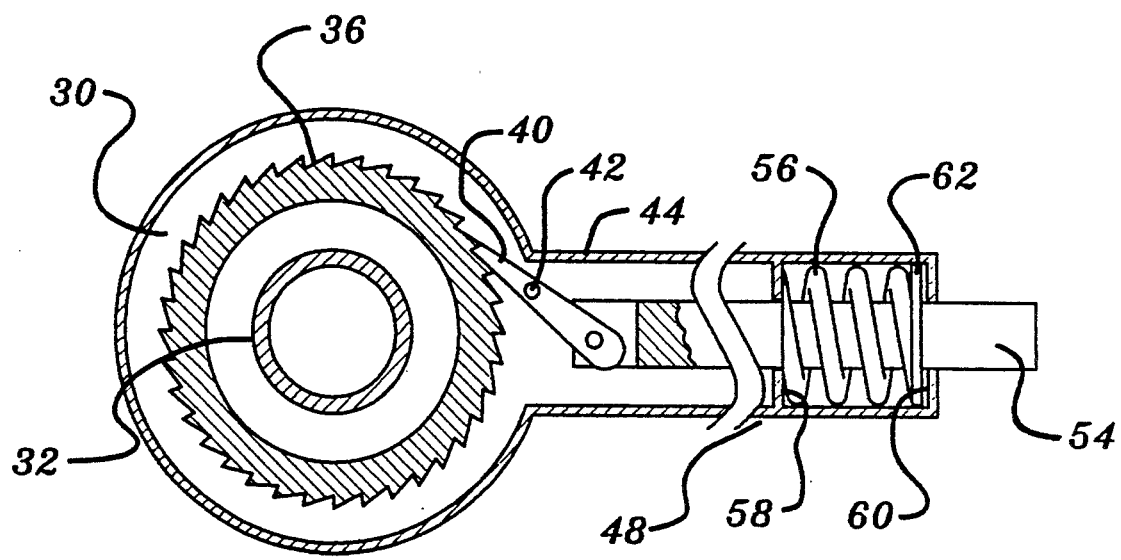
FIG. 6 is a sectional view of the tensioning mechanisms and control means within the traction box of the prior figures.

With reference now to the drawings, and in particular to FIG. 1 thereof, a new and improved surgical traction device embodying the principles and concepts of the present invention and generally designated by the reference numeral 10 will be described.

More specifically, it will be noted that FIG. 1 illustrates the apparatus 10 for applying traction forces to the fingers of a patient during orthoscopic surgery. The invention includes a cradle 12 for the arm, hand and fingers of the patient. The cradle is elongated and of a radiolucent material made of a plastic that can be steam autoclaved. An intermediate plate 14 is secured to one end of the cradle for receiving a clamp 16. The clamp is adapted to releasable secure the cradle to an operating table 18 during surgery.

A traction box 22 is secure to the plate 14 and with respect to the cradle 12. The traction box has wires 24 extending therefrom. Their outboard ends extending over the cradle 12 and are connected to finger traps 26 with an "S" hook. The finger traps function is holding the finger while force (traction) is applied to the fingers of the patient. The inboard ends of the wires extend to within the traction box.

Located within the traction box are tensioning means 30. The tensioning means 30 include a shaft 32 supported about a horizontal axis perpendicular to the axis of the wires. A plurality of spools 34 are mounted for rotation upon the shaft 32. The inboard end of each wire 24 is secured to an associated spool 34. A rachet wheel 36 is coupled to each spool 34 by being mounted on the shaft 32 so that each spool 34 and its associated ratchet wheel 36 may rotate together independent of the supporting shaft 32 and independent of the other spool-ratchet wheel assemblies.

A pawl 40 is operatively coupled to each rachet wheel 36. Each pawl 40 has a pivot rod 42 coupled to a wrench housing 44. The interior end of the pawl couples with the teeth of the ratchet wheel. The exterior end of the pawl is coupled to associated release components.

Control mechanisms are operatively coupled to each spool 34 and rachet wheel 36. The control mechanisms include a wrench 48 to pivot the axis of the pawl about an axis consistent with the axis of the shaft 32. The shaft is fixed through its supporting brackets 50 at opposite ends of traction box 22. The wrench is operator controlled and functions to move the pawl 40 in a reciprocating arcuate path to advance its associated rachet wheel and spool. This action operates to wind up its associated wire and to apply a traction force to a finger of a patient.

The control mechanisms for each spool 34 also include a rod 54 extending through its associated wrench 48. The rod 54 functions to pull the pawl against the action of a spring 56 away from its associated ratchet wheel 36 for releasing the traction whereby a patient's finger maybe released. Each spring 56 is normally maintained in tension between surfaces 58 and 60 integral with the interior of the wrench housing 44. Ring 62 is coupled to the rod 54 to re-engage the pawl 40 with the ratchet wheel teeth after release of the exposed rod end.

A gauge 64 is associated with each spool. The gauge functions to sense and display the tension pressure applied to each finger through its wire, spool and wrench. Each gauge 64 has an interior end 66 secured for rotation on the shaft 32. An exterior end has a pointer 68 normally centered with respect to windows 72 in the traction box 22. Movement of any wrench 48 to wind up its associated wire 24 will apply a force to the interior end 66 whereby the pointer will rotate to create a visible indication of the applied forces by viewing the pointer 68 through the window.

Except for the plastic cradle 12 as described above, all other components of the apparatus are preferably fabricated of a surgical steel or equivalent so that the apparatus may be steam sterilized in an autoclave.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. Apparatus for applying traction forces to the fingers, wrist and forearm of a patient during orthopedic surgery comprising, in combination:
   a cradle for the arm of the patient, the cradle being radiolucent;
   a clamp adapted to releasable secure the cradle to an operating table during surgery;
   a traction box secure with respect to the cradle, the traction box having wires extending therefrom with their outboard ends extending over the cradle and attaching to finger straps, by means of an "S" hook, for holding the fingers of the patient and with their inboard ends extending to within the traction box;
   tensioning means within the traction box, the tensioning means including a shaft supported about a horizontal axis perpendicular to the wires, a plurality of spools mounted for rotation upon the shaft with the inboard end of each wire secured to an associated spool, a rachet wheel coupled to each spool and a pawl operatively coupled to each rachet wheel;
   control means operatively coupled to each spool and rachet wheel, the control means including a wrench to pivot the axis of the pawl about an axis consistent with the axis of the shaft to move the pawl in a reciprocating arcuate path to advance its associated rachet wheel and spool to wind up its associated wire and to apply a traction force to a finger of a patient, each control means also including a rod extending through its associated wrench and a spring mounted on the rod to pull the pawl against the action of the spring away from its rachet wheel for releasing the traction; and
   a gauge associated with each spool to sense and display the pressure applied to each finger through its wire, spool and wrench.

2. Apparatus for applying traction forces to the fingers of a patient during surgery comprising:
   a traction box, the traction box having wires extending therefrom with their outboard ends connecting to a finger trap, by means of an "S" hook, for holding the fingers of the patient and with their inboard ends extending to within the traction box;
   tensioning means within the traction box, the tensioning means including a shaft supported about an axis perpendicular to the wires, a plurality of spools mounted for rotation upon the shaft with the inboard end of each wire secured to an associated spool, a rachet wheel coupled to each spool and a pawl operatively coupled to each rachet; and
   control mechanisms operatively coupled to each spool and rachet wheel the control means including a wrench to pivot the pawl about an axis consistent with the axis of the shaft to move the pawl in a reciprocating arcuate movement to advance its associated rachet wheel and spool to wind up its associated wire for applying a traction force to a finger of a patient.

3. The apparatus as set forth in claim 2 and further including a rod extending through the wrench and a spring mounted on the rod to pull the pawl against the action of the spring away from its associated ratchet wheel for releasing the tractions.

4. The apparatus as set forth in claim 2 and further including a gauge associated with each spool to sense and display the pressure applied to each finger through its associated wire, spool and wrench.

5. The apparatus as set forth in claim 2 wherein the apparatus is constructed and configured to be sterilized.

* * * * *